(12) United States Patent
Foss et al.

(10) Patent No.: US 10,080,363 B2
(45) Date of Patent: Sep. 25, 2018

(54) METHOD FOR GENERATING A HALOGEN-STABLE ANTI-MICROBIAL SYNTHETIC FIBER

(71) Applicant: PURTHREAD TECHNOLOGIES, INC., Cary, NC (US)

(72) Inventors: Stephen Woodrow Foss, Naples, FL (US); Reyad Ilayan Sawafta, Greensboro, NC (US)

(73) Assignee: PurThread Technologies, Inc., Cary, NC (US)

( * ) Notice: Subject to any disclaimer, the term of this patent is extended or adjusted under 35 U.S.C. 154(b) by 179 days.

(21) Appl. No.: 15/175,398

(22) Filed: Jun. 7, 2016

(65) Prior Publication Data

US 2017/0006860 A1     Jan. 12, 2017

Related U.S. Application Data

(60) Continuation of application No. 14/482,123, filed on Sep. 10, 2014, which is a division of application No. 13/276,069, filed on Oct. 18, 2011.

(Continued)

(51) Int. Cl.
*D01D 1/04* (2006.01)
*D01D 5/08* (2006.01)
(Continued)

(52) U.S. Cl.
CPC ............ *A01N 25/10* (2013.01); *A01N 25/34* (2013.01); *A01N 59/16* (2013.01); *A01N 59/20* (2013.01); *B29C 45/0001* (2013.01); *D01F 1/04* (2013.01); *D01F 1/103* (2013.01); *D01F 6/62* (2013.01); *D01F 9/00* (2013.01); *B29K 2067/003* (2013.01); *B29K 2105/0011* (2013.01); *B29K 2105/0032* (2013.01); *Y10T 428/2904* (2015.01); *Y10T 428/298* (2015.01)

(58) Field of Classification Search
CPC .... D01D 1/04; D01D 5/08; D01F 1/04; D01F 1/10; D01F 1/103; D01F 6/62; D04H 3/011
USPC .................................................. 264/103, 211
See application file for complete search history.

(56) References Cited

U.S. PATENT DOCUMENTS 4,578,414 A    3/1986  Sawyer et al.
4,786,556 A    11/1988  Hu et al.
(Continued)

FOREIGN PATENT DOCUMENTS

CN    101705527 A    5/2010
EP    2655709 A2    10/2013
(Continued)

OTHER PUBLICATIONS

Information Disclosure Statement (IDS) Letter Regarding Common Patent Application(s), dated Oct. 6, 2016.
(Continued)

*Primary Examiner* — Leo B Tentoni
(74) *Attorney, Agent, or Firm* — Tillman, Wright & Wolgin; David R. Higgins; Neal B. Wolgin

(57) ABSTRACT

A method for producing fibers with improved color and anti-microbial properties is described. One embodiment includes a method for generating a halogen stable antimicrobial synthetic fiber, the method comprising creating a mixture that includes a polymer, an anti-microbial agent, and a non-halogen pigment, and extruding the mixture to form an anti-microbial synthetic fiber.

13 Claims, 4 Drawing Sheets

Step 100
MIX POLYMER, ANTI-MICROBIAL, AND CATIONIC PIGMENT

Step 200
EXTRUDE MIXTURE TO CREATE FIBER

Step 300
PROCESS FIBER FOR INTENDED END USE

Related U.S. Application Data

(60) Provisional application No. 61/394,242, filed on Oct. 18, 2010.

(51) Int. Cl.

| | | |
|---|---|---|
| *D01F 1/10* | (2006.01) | |
| *D04H 3/011* | (2012.01) | |
| *A01N 25/10* | (2006.01) | |
| *A01N 25/34* | (2006.01) | |
| *D01F 1/04* | (2006.01) | |
| *D01F 6/62* | (2006.01) | |
| *B29C 45/00* | (2006.01) | |
| *D01F 9/00* | (2006.01) | |
| *A01N 59/16* | (2006.01) | |
| *A01N 59/20* | (2006.01) | |
| *B29K 67/00* | (2006.01) | |
| *B29K 105/00* | (2006.01) | |

(56) References Cited

U.S. PATENT DOCUMENTS

| | | |
|---|---|---|
| 4,891,391 A | 1/1990 | McEntee |
| 5,064,599 A | 11/1991 | Ando et al. |
| 5,405,644 A | 4/1995 | Ohsumi et al. |
| 6,384,168 B1 | 5/2002 | Tanaka et al. |
| 6,723,428 B1 | 4/2004 | Foss et al. |
| 6,841,244 B2 | 1/2005 | Foss et al. |
| 6,946,196 B2 | 9/2005 | Foss |
| 8,183,167 B1 | 5/2012 | Delattre et al. |
| 8,193,267 B2 | 6/2012 | Burton et al. |
| 9,878,480 B1 | 1/2018 | Grimes et al. |
| 9,908,987 B2 | 3/2018 | Foss et al. |
| 2003/0204916 A1 | 11/2003 | Green et al. |
| 2004/0018359 A1 | 1/2004 | Haggquist |
| 2004/0096654 A1 | 5/2004 | Morin et al. |
| 2004/0180200 A1 | 9/2004 | Bertamini et al. |
| 2004/0259973 A1 | 12/2004 | Sakuma et al. |
| 2005/0028563 A1 | 2/2005 | Mullins et al. |
| 2005/0054830 A1 | 3/2005 | Islam et al. |
| 2005/0245685 A1 | 11/2005 | Otake et al. |
| 2006/0074154 A1 | 4/2006 | Harashina et al. |
| 2006/0142438 A1 | 6/2006 | Ishii et al. |
| 2006/0246149 A1 | 11/2006 | Buchholz et al. |
| 2006/0252326 A1 | 11/2006 | Mishler |
| 2008/0009586 A1 | 1/2008 | VanSumeren et al. |
| 2008/0063679 A1 | 3/2008 | Sawafta et al. |
| 2008/0090945 A1 | 4/2008 | Langrick et al. |
| 2008/0187603 A1 | 8/2008 | Sawafta |
| 2008/0197528 A1 | 8/2008 | Wood |
| 2008/0242794 A1 | 10/2008 | Sandford et al. |
| 2008/0268011 A1 | 10/2008 | Goldmann et al. |
| 2008/0306181 A1 | 12/2008 | Garey et al. |
| 2009/0068283 A1 | 3/2009 | Sugiura et al. |
| 2009/0130161 A1 | 5/2009 | Sarangapani |
| 2009/0218266 A1 | 9/2009 | Sawafta et al. |
| 2009/0246258 A1 | 10/2009 | Shukla et al. |
| 2009/0269379 A1 | 10/2009 | Herbst |
| 2009/0312456 A1 | 12/2009 | Changping |
| 2010/0124861 A1 | 5/2010 | Wendler et al. |
| 2010/0136073 A1 | 6/2010 | Preuss et al. |
| 2010/0267885 A1 | 10/2010 | Harimoto |
| 2011/0142900 A1 | 6/2011 | Ohta et al. |
| 2012/0083750 A1 | 4/2012 | Sansoucy |
| 2012/0094120 A1 | 4/2012 | Foss et al. |
| 2012/0141723 A1 | 6/2012 | Chuah et al. |
| 2012/0164449 A1 | 6/2012 | Foss |
| 2012/0222826 A1 | 9/2012 | Foss et al. |
| 2013/0152737 A1 | 6/2013 | Chen et al. |
| 2013/0209386 A1 | 8/2013 | Cove et al. |
| 2014/0259721 A1 | 9/2014 | Durdag et al. |
| 2014/0374941 A1 | 12/2014 | Foss et al. |
| 2015/0044449 A1 | 2/2015 | Foss et al. |
| 2015/0147570 A1 | 5/2015 | Foss |
| 2015/0342990 A1 | 12/2015 | Baumann |
| 2017/0044691 A1 | 2/2017 | Foss |

FOREIGN PATENT DOCUMENTS

| | | |
|---|---|---|
| JP | 01-096244 A | 4/1989 |
| JP | 01-139805 A | 6/1989 |
| JP | H02-087004 U | 7/1990 |
| JP | 10-310935 A | 11/1998 |
| JP | 2001-011734 A | 1/2001 |
| JP | 2004-197242 A | 7/2004 |
| JP | 2009-108448 A | 5/2009 |
| KR | 10-0766418 B1 | 10/2007 |
| WO | 2000053413 A1 | 9/2000 |
| WO | 2007078076 A1 | 7/2007 |
| WO | 2008010199 A2 | 1/2008 |
| WO | 2010024423 A1 | 3/2010 |
| WO | 2012088507 A2 | 6/2012 |
| WO | 2012088507 A3 | 10/2012 |
| WO | 2015023644 A2 | 2/2015 |
| WO | 2015184347 A1 | 12/2015 |

OTHER PUBLICATIONS

Sigma-Aldrich, MSDS for Copper (II) phthalocyanine, reprinted Feb. 7, 2013 (6 pages).

Czarnobaj, K. "Sol-gel-processed silica/polydimethylsiloxane/calcium xerogels as polymeric matrices for Metronidazole delivery system." Polym. Bull. 66:223-237 (2011) (15 pages).

"International Search Report" and "Written Opinion" of PCT Application No. PCT/US2014/050666, dated Jan. 22, 2015 (10 pages).

"International Search Report" and "Written Opinion" of PCT Application No. PCT/US2011/067184, dated Aug. 24, 2012 (9 pages).

"European Search Report" for European Application No. 11850293.9, dated Apr. 16, 2014 (7 pages).

"International Preliminary Report on Patentability" under Chapter 1 of the Patent Cooperation Treaty, in International Application No. PCT/US2014/050666, dated Feb. 16, 2016 (7 pages).

Step 100

MIX POLYMER, ANTI-MICROBIAL, AND CATIONIC PIGMENT

Step 200

EXTRUDE MIXTURE TO CREATE FIBER

Step 300

PROCESS FIBER FOR INTENDED END USE

FIGURE 1

METHOD FOR GENERATING A HALOGEN-STABLE ANTI-MICROBIAL SYNTHETIC FIBER

CROSS-REFERENCE TO RELATED APPLICATIONS

The present application is a U.S. continuation patent application of, and claims priority under 35 U.S.C. § 120 to, U.S. nonprovisional patent application Ser. No. 14/482,123, filed Sep. 10, 2014 and now abandoned, which '123 application published on Dec. 25, 2014 as U.S. Patent Application Publication No. US 2014/0374941 A1, which '123 application and its publication are incorporated by reference herein in their entirety, and which '123 application is a U.S. divisional patent application of, and claims priority under 35 U.S.C. § 120 to, U.S. nonprovisional patent application Ser. No. 13/276,069, filed Oct. 18, 2011 and now abandoned, which '069 application published on Apr. 19, 2012 as U.S. Patent Application Publication No. US 2012/0094120 A1, which '069 application and its publication are incorporated by reference herein in their entirety, and which '069 application is a U.S. nonprovisional patent application of, and claims priority under 35 U.S.C. § 119(e) to, U.S. provisional patent application Ser. No. 61/394,242, filed Oct. 18, 2010, which '242 application is incorporated by reference herein in its entirety.

BACKGROUND OF THE PRESENT INVENTION

Field of the Present Invention

The present invention relates to fibers and fabrics designed for the effective destruction of pathogens such as bacteria, mold, mildew, fungus, spores and viruses.

Background

Anti-microbial additives containing copper, silver, gold, and zinc, either individually or combined, have been effective against pathogens such as bacteria, mold, mildew, virus, spores, and fungus. Accordingly, fibers and fabrics have been produced with anti-microbial alloys in various synthetic polymers such as polyester, polypropylene, nylon, rayon, and polylactic acid (PLA). There are many uses and applications for these types of anti-microbial fibers and fabrics, including the healthcare industry, hospitality industry, military, and infant care, among others. However, current anti-microbial fibers and fabrics have shortcomings in meeting the requirements of these uses and applications.

For example, in the healthcare and hospitality industry—such as in a hospital, nursing homes, extended care facilities, hotels, spas or the like—it is required that privacy curtains, isolation gowns, sheets, towels, scrubs, doctor's coats, bath robes, pajamas, and uniforms for medical personnel, both be sanitary and be perceived as sanitary. Therefore, the healthcare and hospitality industries require that these fabrics and garments conform to certain sanitation criteria. As there has been a rise in the possibility of contracting various contagious diseases such as Methicillin-resistant *Staphylococcus aureus* (MRSA) over the past few years, most in the healthcare industry now require bleaching of the towels, garments and other fabrics used in hospitals and various places where repeated use of the towels, garments and fabrics will, or is likely to, occur. This, of course, eliminates many of the types and colors of towels, garments and fabrics that can be used in the healthcare industry and is one reason why most of the fabrics are white. Moreover, because fibers and fabrics produced with known methods lose their effectiveness during repeated launderings with chlorine bleach, the laundering process required in these industries causes issues with known anti-microbial fibers and fabrics.

While the selection of white fabrics can be beneficial because of the repeated launderings, additives of copper, silver, gold, and zinc will discolor the fibers and fabrics during the life of the product, primarily due to oxidation. Accordingly, there is a need to add coloration to hide the undesirable shades created by the oxidation of the additives. In some cases, pigments have been used to color synthetic fibers by adding the pigments to the molten polymer of thermoplastic resins such as polyester, polypropylene, nylon, acrylic, or PLA. But in many cases pigments have been shown to have destructive effects on anti-microbial performance. These destructive effects are only increased due to bleach treatments that are commonly used on sanitary fabrics.

Thus the need exists for an anti-microbial fabric that will resist the destructiveness of washing in chlorine bleach and maintain its color and efficacy against pathogens. Although present fabrics and methods of making fabrics are functional, they are not sufficiently effective or otherwise satisfactory. Accordingly, a system and method are needed to address the shortfalls of present technology and to provide other new and innovative features.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

In an embodiment, the present invention comprises a method for generating a halogen stable anti-microbial synthetic fiber, the method comprising creating a mixture, the mixture comprising a polymer, an anti-microbial agent, and a cationic pigment; and extruding the mixture to form an anti-microbial synthetic fiber. The cationic pigment may also be a non-halogen pigment, include halogen bonding sites that attract chlorine or other halogens known to be detrimental to anti-microbial fibers, and/or include an element with known anti-microbial properties. In certain embodiments, the cationic pigment may be Phthalo Blue. In yet further embodiments, Titanium Dioxide may be added to the mixture with the Phthalo Blue cationic pigment.

In another embodiment, the present invention comprises a synthetic fiber comprising a polymer, an anti-microbial agent, and a cationic pigment. The cationic pigment may also be a non-halogen pigment, include halogen bonding sites, and/or include an element with known anti-microbial properties. In certain embodiments, the cationic pigment may be Phthalo Blue. The synthetic fiber can have a density of 0.4 to 25 denier, and specifically 1.0 to 1.5 denier in some embodiments. The fiber may be in continuous form or cut to a staple length from 0.25" to 7.5" (6 mm to 190 mm), and specifically 1.5" (38 mm) or 2" (51 mm). In yet another embodiment, the fiber may be part of a continuous filament nonwoven fabric, such as a spunbond or spunmelt fabric.

As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

FIG. 1 includes a flow chart for an exemplary method of producing fibers consistent with an embodiment of the present invention;

DETAILED DESCRIPTION

Figure 2:
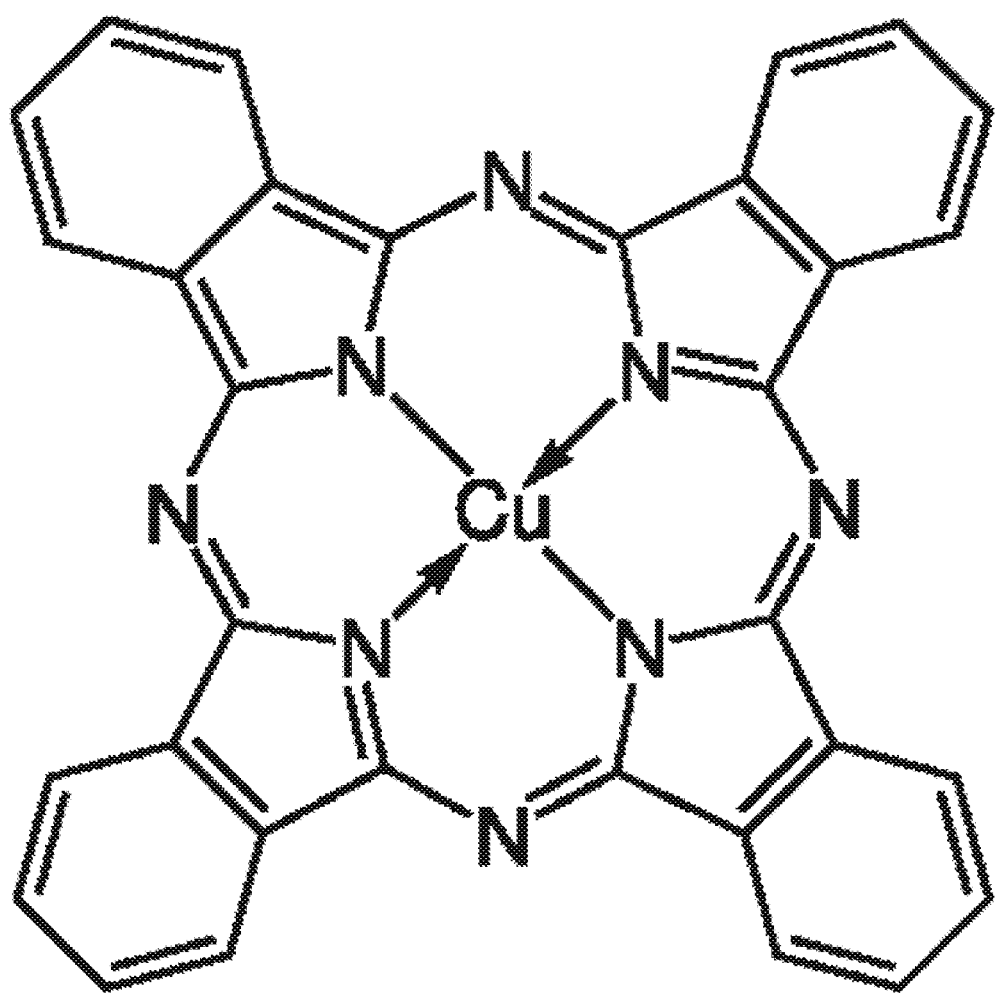
FIG. 2 shows the molecular structure of Phthalo Blue pigment, with the copper molecule at its core.

Referring now to the drawings, where like or similar elements are designated with identical reference numerals throughout the several views, and referring in particular to FIG. 1, it illustrates a method for manufacturing colored fibers with improved anti-microbial performance. At Step 100 a mixture is created, the mixture including a polymer, an anti-microbial alloy powder, and a cationic pigment. As used herein, a polymer refers to a compound suitable for fiber and fabric generation including, but not limited to, a thermoplastic polymer, polyester, nylon, rayon, polyethylene (PE), polypropylene (PP), polyethylene terephthalate (PET), polyethylene terephthalate glycol (PETG), co-PET, polylactic acid (PLA), and polytrimethylene terephthalate (PTT). In a preferred embodiment, the polymer may be polyester for durability, wrinkle resistance and color retention or nylon for its antidrip, slow burn properties.

An anti-microbial agent may be any suitable anti-microbial, such as silver, copper, zinc and/or gold in metallic forms (e.g., particulates, alloys and oxides), salts (e.g., sulfates, nitrates, acetates, citrates, and chlorides) and/or in ionic forms. In some embodiments, the anti-microbial agent is an anti-microbial alloy powder with a particle size of less than 1 micron, and preferably 0.3 to 0.6 micron.

The anti-microbial agent may be comprised of an anti-microbial powder formed from alloys of one or more metals that exhibit anti-microbial properties. Antimicrobial alloys made of two or more element alloys can have superior anti-microbial properties compared to one element particles. Embodiments of the present invention can include an anti-microbial alloy which includes a combination of: transition metals of the periodical table such as chromium, manganese, iron, cobalt, nickel, copper, zinc, silver, and/or gold; rare earth metals from the lanthanides such as cerium, neodymium, samarium, gadolinium, terbium, dysprosium, holmium, and/or erbium; and/or alkali metals such as lithium, sodium, potassium, magnesium, and/or calcium. The combination may comprise a binary combination, ternary combination, quaternary combination, or even higher order combination. The selected alloys, and the relative percentages of each alloy, may be selected depending on the intended use of the fiber or other selection criteria. Different combinations will result in different anti-microbial classes that may be used with the present invention.

For example, different classes of anti-microbial alloys have been produced by QuarTek Corporation as described in various patent applications (U.S. Provisional Application Nos. 60/888,343 and 60/821,497 filed on Aug. 4, 2006 and U.S. patent application Ser. No. 11/868,475 filed on Oct. 6, 2007, Ser. No. 11/858,157 filed on Sep. 20, 2007, and Ser. No. 11/671,675 filed on Feb. 6, 2007). These anti-microbial alloys have been produced by varying the elemental composition of the alloys, the elemental ratios within the same alloy, or by changing parameters in the synthesis process. As needed, these anti-microbial alloys may be synthesized in various size ranges from 5 nm to 2000 nm, preferably less than 1000 nm, or even within the range of 100-500 nm.

A cationic pigment is a pigment which has a positively charged molecular structure. In a preferred embodiment, the cationic pigment is a non-halogen pigment which does not include halogens such as chlorine, bromine or fluorine in its molecular structure. In another embodiment, the cationic pigment further includes halogen bonding sites that can attract chlorine or other halogens that may come into contact with the fiber, such as during laundering. These halogen bonding sites can attract and connect to a chlorine molecule or other halogen molecules and protect the alloys of copper, silver, gold, and/or zinc that provide the anti-microbial properties to the fiber. In yet further embodiments, the cationic pigment may be selected because it comprises an element with known anti-microbial properties.

For example, a preferred cationic pigment is Phthalo Blue Pigment (Phthalocyanine Blue), which has a molecular structure $C_{32}H_{16}CuN_8$ as shown in FIG. 2. Phthalo Blue was chosen because, as shown in FIG. 2, it does not include a halogen, contains a Copper molecule in its core, and has 16 available sites that can attract halogen molecules such as chlorine. A halogen molecule such as chlorine can replace a hydrogen molecule and protect the alloys of copper, silver, gold, and zinc. In addition, Phthalo Blue is a brilliant blue pigment which resists fading due to bleach and sunlight. It has excellent hiding power and prevents any discoloration from the oxidation of copper, silver, or zinc. In some embodiments, Titanium Dioxide may also be added because it has excellent hiding power and softens the strong blue of Phthalo Blue. Titanium Dioxide also does not contain any chlorine molecules.

Other non-halogen pigments that may be selected include:
Egyptian Blue (Calcium Copper Silicate) $CaCuSi_4O_{10}$
Vermillion (Mercury Sulfide) HgS
Iron Oxide Red FeO
Ultramarine Blue $Na_2OSAl_2SiO_6$
Han Purple $BaCuSi_2O_6$
Paris Green (Aceto-arsenite) ($\{CuC_2H_3O_2\}_2$-$3Cu(AsO_2)_2$)
Sheele's Green (Copper Arsenite) $CuHA_5O_5$ As indicated by Step 200 in FIG. 1, once the mixture is created, the mixture may be extruded in order to create a fiber. The extrusion process itself depends on the temperature of the mixture being sufficiently high to melt the mixture. A melting step may be a separate step in FIG. 1 or it may be part of either the mixing process or the extruding process. When the mixture is at a sufficiently high temperature, the mixture may be extruded using conventional mechanisms such as a spinneret. The fiber may then be drawn, crimped, cut and spun into a yarn or other fabric depending on the intended end use (Step 300).

An exemplary fiber consistent with the present invention was made with between 99.3% and 99.6% Polyester (PET) resin, between 0.1% and 0.4% QuarTek Alloy QSM-ACL73 and 0.3% Phthalo Blue pigment. In some embodiments, Titanium Dioxide may also be added. The compounds were extruded at a melt temperature of 290° C. and pumped through a 2400 hole spinneret to produce a fiber of 5.5 denier. The fiber was then drawn to 1.5 denier, crimped, and cut to 1.5" (38 mm). These exemplary fibers exhibit improved visual properties and improved anti-microbial effectiveness after launderings. Fibers produced with these pigments had very poor anti-microbial properties.

Figure 3:
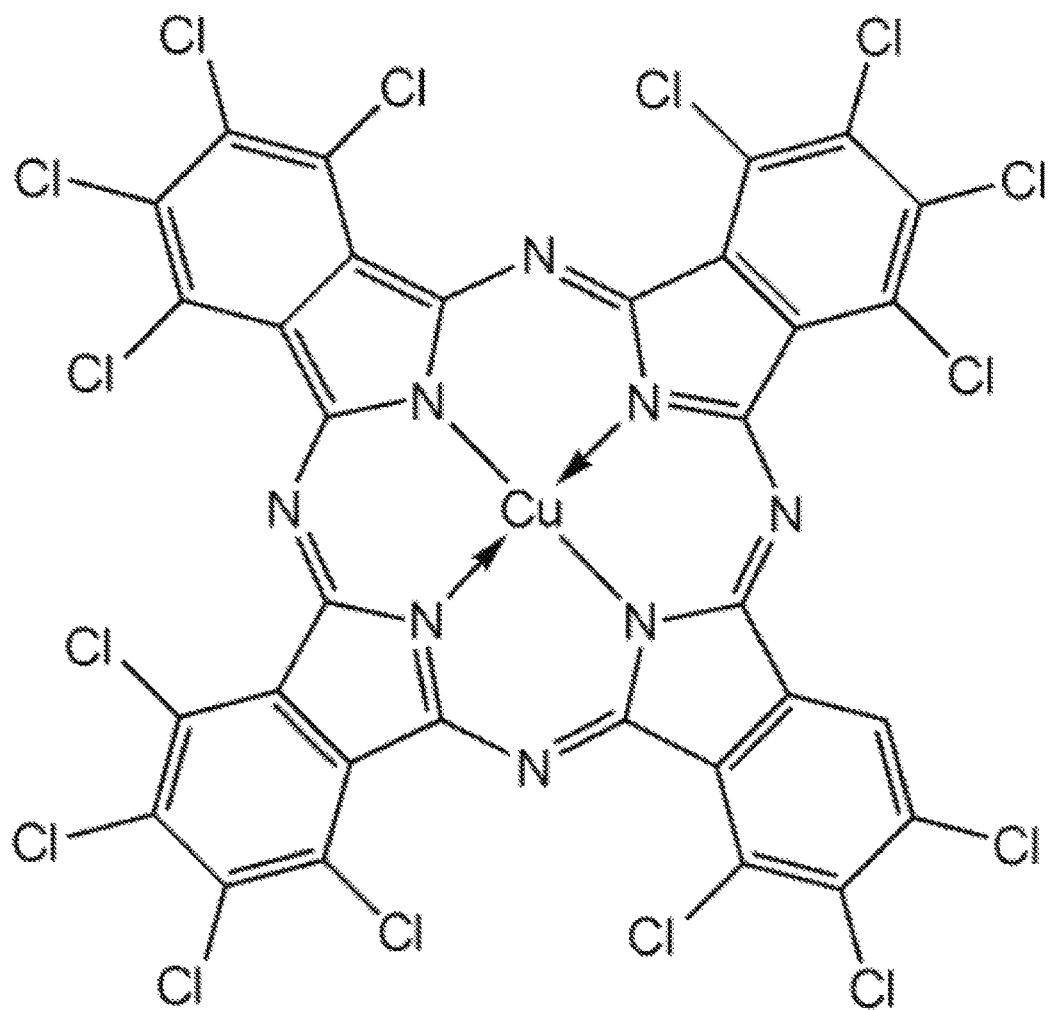
FIG. 3 shows the molecular structure of Phthalocyanine Green G pigment with 15 chlorine molecules.
Figure 4:
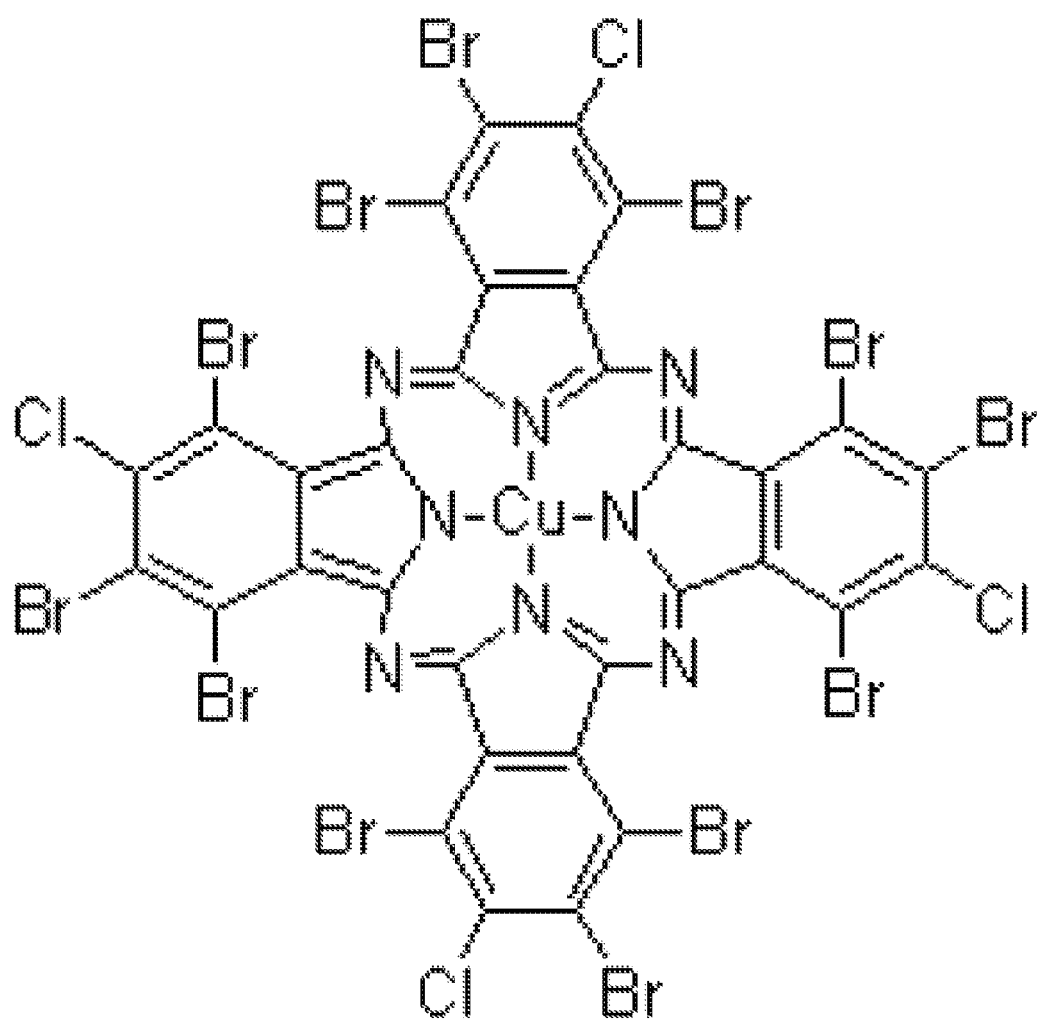
FIG. 4 shows the molecular structure of Phthalo Green 36 pigment with a combination of 16 chlorine and bromine molecules.

In accordance with the present method, pigments such as Phthalocyanine Green G (molecular structure is shown in FIG. 3) and Phthalo Green 36 (molecular structure is shown in FIG. 4) will not be used because they contain chlorine molecules which adversely affect the anti-microbial properties of a resultant fiber.

In conclusion, the present invention provides, among other things, method for producing fibers with improved color and anti-microbial properties. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A method for generating a halogen-stable anti-microbial synthetic fiber, the method comprising:
   creating a mixture comprising:
      a base polymer comprised at least predominantly of polyester in pellet form;
      an anti-microbial agent in the form of an alloy powder that includes a combination of transition metals;
      a cationic non-halogen pigment that includes halogen bonding sites; and
      titanium dioxide for softening a hue of the non-halogen pigment;
   heating the mixture to a melt temperature; and
   extruding the mixture to form an anti-microbial synthetic fiber;
   wherein the cationic non-halogen pigment is adapted to attract and bond with halogenic molecules at the halogen bonding sites, thereby shielding the anti-microbial agent from degradation arising from interactions with halogenic molecules.

2. The method of claim 1, wherein the cationic non-halogen pigment comprises an element with known anti-microbial properties.

3. The method of claim 1, wherein the cationic non-halogen pigment is phthalo blue.

4. The method of claim 1, wherein the cationic non-halogen pigment is selected from the group consisting of $CaCuSi_4O_{10}$, HgS, FeO, $Na_2OSAl_2SiO_6$, $BaCuSi_2O_6$, $(\{CuC_2H_3O_2\}_2\text{-}3Cu(AsO_2)_2)$, and $CuHA_5O_5$.

5. The method of claim 1, wherein the combination is a binary combination of transition metals.

6. The method of claim 1, wherein the combination is a ternary combination of transition metals.

7. The method of claim 1, wherein the combination is a quaternary combination of transition metals.

8. A method for generating a halogen-stable anti-microbial fabric material, the method comprising:
   creating a mixture comprising:
      a base polymer comprised at least predominantly of polyester in pellet form;
      an anti-microbial agent in the form of an alloy powder that includes a combination of transition metals; and
      a cationic non-halogen pigment that includes halogen bonding sites;
   heating the mixture to a melt temperature;
   extruding the mixture to form an anti-microbial synthetic fiber; and
   using the anti-microbial synthetic fiber to create a halogen-stable anti-microbial fabric;
   wherein the cationic non-halogen pigment is adapted to attract and bond with halogenic molecules at the halogen bonding sites, thereby shielding the anti-microbial agent from degradation arising from interactions with halogenic molecules.

9. The method of claim 8, wherein the cationic non-halogen pigment comprises an element with known anti-microbial properties.

10. The method of claim 8, wherein the cationic non-halogen pigment is phthalo blue.

11. The method of claim 8, wherein the cationic non-halogen pigment is selected from the group consisting of $CaCuSi_4O_{10}$, HgS, FeO, $Na_2OSAl_2SiO_6$, $BaCuSi_2O_6$, $(\{CuC_2H_3O_2\}_2\text{-}3Cu(AsO_2)_2)$, and $CuHA_5O_5$.

12. The method of claim 8, wherein the mixture further comprises titanium dioxide for softening a hue of the non-halogen pigment.

13. The method of claim 8, wherein the combination is a binary combination of transition metals.

* * * * *